United States Patent [19]

Hoff

[11] Patent Number: 5,114,956
[45] Date of Patent: May 19, 1992

[54] PARENTERAL FORMULATION OF NIMODIPINE

[75] Inventor: Dieter Hoff, Leverkusen, Fed. Rep. of Germany

[73] Assignee: Bayer Aktiengesellschaft, Leverkusen, Fed. Rep. of Germany

[21] Appl. No.: 641,323

[22] Filed: Jan. 15, 1991

Related U.S. Application Data

[63] Continuation of Ser. No. 599,037, Apr. 11, 1984, abandoned.

[30] Foreign Application Priority Data

May 6, 1983 [DE] Fed. Rep. of Germany ....... 3316510

[51] Int. Cl.$^5$ ............................................. A61K 31/44
[52] U.S. Cl. ................................................. 514/356
[58] Field of Search ......................................... 514/356

[56] References Cited

U.S. PATENT DOCUMENTS

| | | | |
|---|---|---|---|
| 4,154,839 | 5/1979 | Wehinger et al. | 424/266 |
| 4,166,855 | 9/1979 | Wehinger et al. | 424/266 |
| 4,256,749 | 3/1981 | Horstmann et al. | 424/251 |

FOREIGN PATENT DOCUMENTS 2018134 10/1979 United Kingdom ................ 514/356

OTHER PUBLICATIONS

*Husa's Pharmaceutical Dispensing*, Mack Pub. Co., Easton, Pa., (1966), pp. 400-401.
*Pharmaceutical Sciences*, (1980), Mack Pub. Co., Easton, Pa., p. 1467.
*Chem. Abstracts*, vol. 92 (1980) 220691r.

Primary Examiner—Frederick E. Waddell
Assistant Examiner—Kimberly R. Jordan
Attorney, Agent, or Firm—Sprung Horn Kramer & Woods

[57] ABSTRACT

A parenteral formulation comprising about
a) 0.01-0.4% by weight of nimodipine, relative to 100 parts by weight of a solvent comprising about
b)
  30-70% by weight of water
  15-40% by weight of propylene glycol and/or polyethylene glycol, and
  15-30% by weight of ethanol and, where appropriate, customary auxiliaries and/or additives.

2 Claims, No Drawings

PARENTERAL FORMULATION OF NIMODIPINE

This application is a continuation of application Ser. No. 599,037, filed Apr. 11, 1984, now abandoned.

The invention relates to a parenteral formulation of nimodipine in a solvent, a process for its preparation and its use for controlling diseases.

Nimodipine is a dihydropyridine derivative having the name 3-β-methoxyethyl 5-isopropyl 1,4-dihydro-2,6-dimethyl-4-(3-nitrophenyl)pyridine-3,5-dicarboxylate which is disclosed in German Offenlegungsschrift 2,815,578. The use of nimodipine for the treatment of disturbances of cerebral blood flow is likewise clear from the Offenlegungsschrift mentioned.

There is a need to make parenteral formulations of nimodipine available in medicine, since unconscious or anaesthetised patients are unable in this condition themselves to take an active compound.

Thus the invention relates to parenteral formulations containing nimodipine, characterized in that they contain:

a) 0.01–0.4% by weight of nimodipine, relative to 100 parts by weight of a solvent consisting of b)
- 30–70% by weight, preferably 45–70% by weight, of water,
- 15–40% by weight, preferably 15–30% by weight, of propylene glycol and/or polyethylene glycol, preferably with a mean molecular weight of 200, 400 and 600,
- 15–30% by weight, preferably 15–25% by weight, of ethanol, and, where appropriate, customary auxiliaries and/or additives.

The term parenteral is particularly understood to include intravenous, intraarterial and intracisternal.

Since nimodipine is photosensitive in bright sunlight, it can prove to be necessary to add colorants to the solution to protect from light and for the purpose of stabilization. Examples of suitable colorants may be apocarotenal, canthaxanthine, tartrazine (E 102), amaranth (E 123) and erythrosine (E 127), but particularly yellow-orange S (E 110). The concentration of the particular colorant, when employed, is 0.01–0.5% by weight, preferably 0.1–0.4% by weight, relative to the solution.

Protection from light is also possible by making injection vials or ampules, instead of the solution, opaque to light so that there is no, or hardly any, penetration by light of a particular wavelength.

The preparation of the formulation according to the invention can be carried out by first dissolving nimodipine in the solvents ethanol, propylene glycol and/or polyethylene glycol, and then adding water.

It can be necessary to add customary stabilizers to the solution to stabilize it, for example tertiary sodium citrate at 0.15–2.5, preferably 1.8–2.2, % by weight and/or citric acid at 0.2–0.6, preferably 0.2–0.5, % by weight relative to 100 parts by weight of solvent.

The formulation according to the invention is suitable for the treatment of acute disturbances of cerebral blood flow, such as, for example, ischaemic neurological deficits following cerebral vasospasms, craniocerebral trauma, ischaemic cerebral damage or cerebral resuscitation.

In general, it has proved advantageous for achieving effective results to administer nimodipine on intravenous administration, in amounts of about 0.5–4 mg per hour, preferably 1–3 mg per hour, on intraarterial administration, in amounts of about 0.05–0.5 mg per hour, preferably 0.1–0.25 mg per hour, and on intracisternal administration, in amounts of about 100 to 300 micrograms.

Where appropriate, it can be necessary to deviate from the amounts mentioned, and in particular to do so as a function of the body weight, but also by reason of the individual response to the medicament or the time or interval over which the administration takes place. Thus it can suffice in some cases to manage with less than the abovementioned minimum amount, while in other cases the abovementioned upper limit must be exceeded.

EXAMPLES

| | | |
|---|---|---|
| 1. | Nimodipine | 0.200 g |
| | 96% ethanol | 200.000 g |
| | Polyethylene glycol 400 | 170.000 g |
| | Tertiary sodium citrate | 2.000 g |
| | Citric acid | 0.300 g |
| | Water for injection | 622.300 g |
| | | 994.800 g |
| 2. | Nimodipine | 0.200 g |
| | 96% ethanol | 150.000 g |
| | Polyethylene glycol 400 | 220.000 g |
| | Tertiary sodium citrate | 2.000 g |
| | Citric acid | 0.300 g |
| | Water for injection | 624.800 g |
| | | 997.300 g |
| 3. | Nimodipine | 0.200 g |
| | 96% ethanol | 220.000 g |
| | Polyethylene glycol 400 | 190.000 g |
| | Tertiary sodium citrate | 2.000 g |
| | Citric acid | 0.300 g |
| | Water for injection | 584.000 g |
| | | 996.500 g |
| 4. | Nimodipine | 0.200 g |
| | 96% ethanol | 150.000 g |
| | Polyethylene glycol 400 | 250.000 g |
| | Tertiary sodium citrate | 2.000 g |
| | Citric acid | 0.300 g |
| | Water for injection | 596.400 g |
| | | 998.900 g |
| 5. | Nimodipine | 0.200 g |
| | 96% ethanol | 150.000 g |
| | Polyethylene glycol 400 | 300.000 g |
| | Tertiary sodium citrate | 2.000 g |
| | Citric acid | 0.300 g |
| | Water for injection | 547.400 g |
| | | 999.900 g |
| 6. | Nimodipine | 0.200 g |
| | 96% ethanol | 170.000 g |
| | Polyethylene glycol 200 | 200.000 g |
| | Tertiary sodium citrate | 2.000 g |
| | Citric acid | 0.300 g |
| | Water for injection | 621.850 g |
| | | 994.350 g |
| 7. | Nimodipine | 0.200 g |
| | 96% ethanol | 190.000 g |
| | Polyethylene glycol 200 | 230.000 g |
| | Tertiary sodium citrate | 2.000 g |
| | Citric acid | 0.300 g |
| | Water for injection | 574.400 g |
| | | 996.900 g |
| 8. | Nimodipine | 0.200 g |
| | 96% ethanol | 200.000 g |
| | Polyethylene glycol 200 | 200.000 g |
| | Tertiary sodium citrate | 2.000 g |
| | Citric acid | 0.300 g |
| | Water for injection | 599.440 g |
| | | 1,001.940 g |
| 9. | Nimodipine | 0.200 g |
| | 96% ethanol | 200.000 g |

| | -continued | |
|---|---|---|
| | Polyethylene glycol 600 | 170.000 g |
| | Tertiary sodium citrate | 2.000 g |
| | Citric acid | 0.300 g |
| | Water for injection | 622.300 g |
| | | 994.800 g |
| 10. | Nimodipine | 0.200 g |
| | 96% ethanol | 200.000 g |
| | Polyethylene glycol 600 | 270.000 g |
| | Tertiary sodium citrate | 2.000 g |
| | Citric acid | 0.300 g |
| | Water for injection | 532.900 g |
| | | 1,005.400 g |
| 11. | Nimodipine | 0.200 g |
| | 96% ethanol | 200.000 g |
| | 1,2-propylene glycol | 220.000 g |
| | Tertiary sodium citrate | 2.000 g |
| | Citric acid | 0.300 g |
| | Water for injection | 579.480 g |
| | | 1,001.980 g |
| 12. | Nimodipine | 0.200 g |
| | 96% ethanol | 150.000 g |
| | 1,2-propylene glycol | 300.000 g |
| | Tertiary sodium citrate | 2.000 g |
| | Citric acid | 0.300 g |
| | Water for injection | 554.800 g |
| | | 1,007.300 g |

CLINICAL RESULTS

Marked prevention of neurological deficits resulting from cerebral vasospasms and reduction in mortality were found on prophylactic intraoperative intracisternal administration of 200 μg of nimodipine followed by several days of continuous intravenous infusion of 1-3 mg of nimodipine per hour to patients with subarachnoid haemorrhage. No neurological deficits occurred in a series of 70 patients, and no patient died. In contrast, in past comparison groups of similar composition, 10-32% of the patients are reported as having severe ischaemic complications which may lead to death.

In a second trial series, in which nimodipine was infused intravenously in doses of 0.5-3 mg per hour to treat neurological deficits following cerebral vasospasms after subarachnoid haemorrhage, the mortality was 18%, while a mortality of 20-50% is reported in the literature for this clinical picture. Although the patients were selected by adverse criteria, two-thirds of the patients had completely recovered or markedly improved by the end of treatment.

Example 1 was used as the basis for the investigations.

It is understood that the specification and examples are illustrative but not limitative of the present invention and that other embodiments within the spirit and scope of the invention will suggest themselves to those skilled in the art.

I claim:

1. A method of making a parenteral formulation consisting essentially of about
   a) 0.01-0.4% by weight of nimodipine, relative to 100 parts by weight of a solvent consisting essentially of about
   b) 15-40% by weight of polyethylene glycol, 15-30% by weight of ethanol, and water, which comprises dissolving the nimodipine in the polyethylene glycol and ethanol, and then adding the water to the solution.

2. A method of making a parenteral formulation consisting essentially of about
   a) 0.01-0.4% by weight of nimodipine, relative to 100 parts by weight of a solvent consisting essentially of about,
   b) 15-30% by weight of polyethylene glycol, 15-25% by weight of ethanol, and water, which comprises dissolving the nimodipine in the polyethylene glycol and ethanol, and then adding the water to the solution.

* * * * *